United States Patent
Guo (10) Patent No.: US 11,098,280 B2
(45) Date of Patent: Aug. 24, 2021

(54) SERUM-FREE CULTURE MEDIUM AND PREPARATION METHOD AND APPLICATION THEREFOR

(71) Applicants: Lei Guo, Beijing (CN); Cheng Li, Beijing (CN)

(72) Inventor: Lei Guo, Beijing (CN)

(73) Assignees: Guo Lei; Li Cheng

( * ) Notice: Subject to any disclaimer, the term of this patent is extended or adjusted under 35 U.S.C. 154(b) by 333 days.

(21) Appl. No.: 16/061,232

(22) PCT Filed: Dec. 11, 2015

(86) PCT No.: PCT/CN2015/097148
§ 371 (c)(1),
(2) Date: Jun. 11, 2018

(87) PCT Pub. No.: WO2017/096616
PCT Pub. Date: Jun. 15, 2017

(65) Prior Publication Data
US 2018/0362920 A1   Dec. 20, 2018

(51) Int. Cl.
*C12N 5/00* (2006.01)
*C12N 5/0775* (2010.01)

(52) U.S. Cl.
CPC ......... *C12N 5/0037* (2013.01); *C12N 5/0665* (2013.01); *C12N 2500/32* (2013.01); *C12N 2500/44* (2013.01); *C12N 2500/90* (2013.01); *C12N 2501/115* (2013.01)

(58) Field of Classification Search
CPC ............... C12N 5/0037; C12N 5/0665; C12N 2500/44; C12N 2501/115; C12N 2500/90; C12N 2500/32
See application file for complete search history.

(56) References Cited

U.S. PATENT DOCUMENTS 6,372,494 B1 *  4/2002  Naughton .............. A61K 35/36
                                                                    435/391
2013/0302285 A1  11/2013  Fong et al.

FOREIGN PATENT DOCUMENTS

CN      103805562 A    5/2014
WO      2012018307 A1  2/2012

OTHER PUBLICATIONS

Yang et al. Conditioned Media from Human Adipose Tissue-Derived Mesenchymal Stem Cells and Umbilical Cord-Derived Mesenchymal Stem Cells Efficiently Induced the Apoptosis and Differentiation in Human Glioma Cell Lines In Vitro. BioMed Research International. vol. 2014, Article ID 109389, 13 pages (Year: 2014).*
Xiao et al. Differentiation of Schwann-like cells from human umbilical cord blood mesenchymal stem cells in vitro. Molecular Medicine Reports 11: 1146-1152, 2015 (Year: 2015).*
Leng et al. Molecular imaging for assessment of mesenchymal stem cells mediated breast cancer therapy. Biomaterials. jUN. 2014; 35(19): 5162-5170. (Year: 2014).*
Jung et al. Ex Vivo Expansion of Human Mesenchymal Stem Cells in Defined Serum-Free Media. Stem Cell International. p. 1-21. (Year: 2012).*
Chen et al. Human Umbilical Cord-Derived Mesenchymal Stem Cells Do Not Undergo Malignant Transformation during Long-Term Culturing in Serum-Free Medium. PLOS ONE. p. 1-8 (Year: 2014).*
Montes et al. Feeder-free maintenance of hESCs in mesenchymal stem cell-conditioned media: distinct requirements for TGF-⊕ and IGF-II. Cell Research 19:698-709 (Year: 2009).*
International Search Report dated Sep. 14, 2016 for corresponding PCT Application No. PCT/CN2015/097148, with English translation (6 pages).
Machine English translation of CN 103805562 A (1 page).
Wang, Qian et al., "Sustaining Effect of Cultured Adult Marrow Mesenchymal Stem Cells Supernatant on Culture and Proliferation of Mesenchymal Stem Cells from Human Umbilical Cord Blood in Vitro", Medical Journal of National Defending Forces in Northwest China, vol. 27, No. 6, Dec. 31, 20016, with English Translation (5 pages).
Zhao, Wei et al., "Sustaining Effect of Cultured Adult Adipose Tissue-Derived Mesenchymal Stem Cells Supernatant on Culture and Proliferation of Mesenchymal Stem Cells from Human Umbilical Cord Blood in Vitro", Journal of Mudanjiang Medical University, vol. 31, No. 4, Aug. 31, 2010, with English Translation (4 pages).
Zhao, Xia et al., "Differences of Human Umbilical Cord Blood-Derived Mesenchymal Stems Cells Cultured in Different Media", Journal of Clinical Rehabilitative Tissue Engineering Research, vol. 17, No. 19, May 7, 2013, with English Translation (9 pages).

* cited by examiner

*Primary Examiner* — Taeyoon Kim
(74) *Attorney, Agent, or Firm* — Lewis Roca Rothgerber Christie LLP (57) ABSTRACT

Provided is a serum-free culture medium, the ingredients of the culture medium comprising 0.05-0.2 parts by volume of β-mercaptoethanol, 0.5-2 parts by volume of non-essential amino acid aqueous solution, 4-6 parts by volume of human mesenchymal stem cell culture supernatant concentrate, and 90-95 parts by volume of a-MEM/DMEM-F12 and recombinant human alkaline fibroblast growth factor of a final concentration of 5-5 ng/ml. The present culture medium is used for carrying out stem cell culture.

5 Claims, 8 Drawing Sheets

Diameter (μm)

SERUM-FREE CULTURE MEDIUM AND PREPARATION METHOD AND APPLICATION THEREFOR

CROSS-REFERENCE TO RELATED APPLICATION(S)

This application is a National Phase Patent Application of International Patent Application Number PCT/CN2015/097148, filed on Dec. 11, 2015. The entire contents of which are incorporated herein by reference.

TECHNICAL FIELD

The present invention relates to the field of stem cell research. Particularly, the present invention relates to a novel, high efficient serum-free culture medium and preparation method and application therefor.

BACKGROUND OF THE INVENTION

Mesenchymal stem cells are ubiquitous in many tissues and organs of human body, and have multi-directional differentiation potential. They have functions of stimulating tissue regeneration, and regulating immunity, and have a broad application prospect in the field of cell therapy. Previous studies show that although bone marrow mesenchymal stem cells have been widely used in clinical, umbilical cord-derived mesenchymal stem cells can not only be ideal substitutes for bone marrow mesenchymal stem cells, but also have a greater potential for application. Human umbilical cord mesenchymal stem cells (hUC-MSCs) derived from human umbilical cord express a variety of special markers for embryonic stem cells, and are characterized by great potential for differentiation, strong proliferative ability, low immunogenicity, convenient material acquisition, having no restrictions on ethical and ethical issues and easy industrialization, etc. Meanwhile, it have been demonstrated in studies that hUC-MSCs have good therapeutic effects in animal models and clinical studies of diseases selected from the group of neurological diseases, the immune system diseases, endocrine system diseases, cancer and heart disease and the like. Thus, hUC-MSCs are possible to be the most clinically promising pluripotent stem cells.

The most important thing to further apply hUC-MSCs to clinic is that, the hUC-MSCs could be expanded abundantly in vitro to reach an effective clinical therapeutic dose. In this regard, culturing hUC-MSCs in vitro has become one of the most fundamental and important technologies. Current medium used in methods for culturing hUC-MSCs is generally basic medium supplemented with FBS, penicillin and streptomycin. However, non-human serum has complex components and may make hUC-MSCs prone to differentiate easily during long-term culture, and there is also a danger of transmitting xenogeneic pathogens by use of non-human serum.

In addition, although various types of serum substitutes have been developed by researchers, cultivation with commercially available serum substitutes and complete culture media for hUC-MSCs is still not ideal, especially, the serum substitutes and complete culture media fail to achieve desired results on adherence and proliferation of stem cells, maintenance of cell stability after long-term culture, and other properties.

SUMMARY OF THE INVENTION

In view of the above technical problems, the inventors of the present invention have found in research that a variety of factors and proteins and the like beneficial to cell growth can be secreted by hUC-MSCs during being cultured, and a long-term expansion culture of cells, particularly stem cells can be conducted under serum-free conditions by use of those factors and proteins.

Therefore, one purpose of the present invention is to provide a serum-free medium comprising a concentrate obtained from a cell culture, and the serum-free medium is particularly suitable for culturing cells under serum-free conditions.

Another purpose of the present invention is to provide a method for preparing the serum-free medium.

Yet another purpose of the present invention is to provide a use of the serum-free medium in the preparation of an agent for stem cell culture.

Technical solutions provided by the present invention are as follows.

In one aspect, the present invention provides a serum-free medium comprising a-MEM/DMEM-F12, β-mercaptoethanol, non-essential amino acids, recombinant human basic fibroblast growth factor (b-FGF) and a concentrate of culture supernatant of human umbilical cord mesenchymal stem cells (hUC-MSCs).

Preferably, the serum-free medium comprises 0.05-0.2 parts by volume of β-mercaptoethanol, 0.5-2 parts by volume of aqueous solution of non-essential amino acids, 4-6 parts by volume of the concentrate of culture supernatant, 90-95 parts by volume of a-MEM/DMEM-F12 and the recombinant human basic fibroblast growth factor at a final concentration of 5-15 ng/ml, and the aqueous solution of non-essential amino acids comprises glycine, alanine, L-asparagine, L-aspartic acid, glutamic acid, proline and serine each at a concentration of 8-12 mM.

More preferably, the serum-free medium comprises 0.1 part by volume of β-mercaptoethanol, 1 part by volume of aqueous solution of non-essential amino acids, 5 parts by volume of the concentrate of culture supernatant, 94 parts by volume of a-MEM/DMEM-F12 and the recombinant human basic fibroblast growth factor at a final concentration of 10 ng/ml.

The concentrate of culture supernatant is produced by a method including the following steps: collecting culture supernatant of human umbilical cord mesenchymal stem cells, and performing centrifugation, filtration through a microfiltration membrane and ultrafiltration concentration successively.

Preferably, the concentrate of culture supernatant is produced by a method including the following steps:

(1) inoculating human umbilical cord mesenchymal stem cells in a serum-free medium at a density of $0.5\text{-}4\times10^4$ cells/cm$^2$ and culturing the cells for 48-72 hours to allow the cells to reach 70%-90% confluence, and then collecting fresh culture supernatant of the umbilical cord mesenchymal stem cells;

(2) centrifuging the culture supernatant at 3000-5000 g for 15-40 min at 4° C., to remove cells and cellular debris suspended therein;

(3) centrifuging the supernatant obtained from step (2) at 10000 g for 30-60 min at 4° C., to remove cytoplasm and other impurities therein;

(4) filtering the supernatant obtained from step (3) through a 0.22 μm microfiltration membrane, to sterilize the supernatant;

(5) transferring the filtrate obtained from step (4) to a 3 KD ultrafiltration concentrator tube, and centrifuging at 3000-4500 g for 60-90 min at 4° C., to concentrate the filtrate to 1/20 to 1/50 of its original volume;

(6) adjusting the concentrate obtained from step (5) with PBS to get a final volume of 1/20 of the volume of the culture supernatant collected in step (1).

In step (1), the human umbilical cord mesenchymal stem cells (hUC-MSCs) are preferably human umbilical cord mesenchymal stem cells isolated from a fresh umbilical cord tissue of a healthy newborn by natural or cesarean section delivery.

And preferably, the serum-free medium in step (1) comprises a-MEM/DMEM-F12, β-mercaptoethanol, non-essential amino acids, recombinant human basic fibroblast growth factor (b-FGF) and optionally a concentrate of culture supernatant of human umbilical cord mesenchymal stem cells; more preferably, the serum-free medium in step (1) comprises 0.05-0.2 parts by volume of β-mercaptoethanol, 0.5-2 parts by volume of aqueous solution of non-essential amino acids, optionally 4-6 parts by volume of the concentrate of culture supernatant, 90-95 parts by volume of a-MEM/DMEM-F12 and the recombinant human basic fibroblast growth factor at a final concentration of 5-15 ng/ml, and the aqueous solution of non-essential amino acids comprises glycine, alanine, L-asparagine, L-aspartic acid, glutamic acid, proline and serine each at a concentration of 8-12 mM; more preferably, the serum-free medium in step (1) comprises 0.1 part by volume of β-mercaptoethanol, 1 part by volume of aqueous solution of non-essential amino acids, optionally 5 parts by volume of the concentrate of culture supernatant, 94 parts by volume of a-MEM/DMEM-F12 and the recombinant human basic fibroblast growth factor at a final concentration of 10 ng/ml.

In another aspect, the present invention provides a method for preparing the serum-free medium, and the method includes:

collecting culture supernatant of human umbilical cord mesenchymal stem cells, and performing centrifugation, filtration through a microfiltration membrane and ultrafiltration concentration successively, to obtain a concentrate of culture supernatant;

preparing a premixture using β-mercaptoethanol, non-essential amino acids and a-MEM/DMEM-F12; and mixing the concentrate of culture supernatant, the premixture and recombinant human basic fibroblast growth factor.

The concentrate of culture supernatant is preferably produced by a method including the following steps:

(1) inoculating human umbilical cord mesenchymal stem cells in a serum-free medium at a density of $0.5\text{-}4\times10^4$ cells/cm$^2$ and culturing the cells for 48-72 hours to allow the cells to reach 70%-90% confluence, and then collecting fresh culture supernatant of the umbilical cord mesenchymal stem cells;

(2) centrifuging the culture supernatant at 3000-4500 g for 15-40 min at 4° C., to remove cells and cellular debris suspended therein;

(3) centrifuging the supernatant obtained from step (2) at 10000 g for 30-60 min at 4° C., to remove cytoplasm and other impurities therein;

(4) filtering the supernatant obtained from step (3) through a 0.22 μm microfiltration membrane, to sterilize the supernatant;

(5) transferring the filtrate obtained from step (4) to a 3 KD ultrafiltration concentrator tube, and centrifuging at 3000-4500 g for 60-90 min at 4° C. to concentrate the filtrate to 1/20 to 1/50 of its original volume;

(6) adjusting the concentrate obtained from step (5) with PBS to get a final volume of 1/20 of the volume of the culture supernatant collected in step (1).

In yet another aspect, the present invention provides a use of the serum-free medium in the preparation of an agent for stem cell culture.

The stem cells are isolated from tissue or organ of a mammal, such as human, which are one or more selected from bone marrow, umbilical cord and fat; preferably, the stem cells are umbilical cord mesenchymal stem cells of mammalian origin; more preferably, the stem cells are umbilical cord mesenchymal stem cells of human origin; most preferably, the stem cells are human umbilical cord mesenchymal stem cells isolated from a fresh umbilical cord tissue of a healthy newborn by natural or cesarean section delivery.

Researches by the inventors have found that a variety of factors and proteins and the like beneficial to cell growth can be secreted by human umbilical cord mesenchymal stem cells during their culture. On this basis, a novel serum-free medium is provided by use of a concentrate obtained through concentrating the culture supernatant of the human umbilical cord mesenchymal stem cells. By utilizing the present medium, a long-term expansion culture of stem cells can be conducted under serum-free conditions, and the stem cells can maintain multipotency and a strong proliferation capacity during the expansion culture. The stem cells can be cells from one or more of bone marrow, umbilical cord and fat derived from a mammal (for example, human), especially umbilical cord mesenchymal stem cells isolated from the umbilical cord of a newborn.

Specifically, the novel serum-free medium provided by the present invention contains no serum components, thereby avoiding instability of the cell growth during the culture resulted from batch difference of the serum, and excluding the possibility of transmitting xenogeneic pathogens. Meanwhile, the application of the present serum-free medium solves problems of poor adherence and slow proliferation of cells in conventional serum-free culture, and the cells cultured can maintain good proliferation and multi-directional differentiation potential during long-term culture. Therefore, the present invention provides an efficient solution for animal cell culture in vitro. In addition, the culture supernatant is a waste of cell culture per se, and its recycling reduces the cost of cell culture.

BRIEF DESCRIPTION OF THE DRAWINGS

Hereinafter, embodiments of the present invention will be described with reference to the accompanying drawings in detail, in which.

DETAILED DESCRIPTION OF PREFERRED EMBODIMENTS

The present invention will be further described in detail in combination with the embodiments hereinafter. It will be appreciated by those skilled in the art that the embodiments provided are only used to illustrate the present invention, rather than limiting the scope of the present invention in any way.

Experimental methods in the following embodiments, if no any other special instruction is provided, are all conducted under conventional conditions or the conditions recommended by the instrument and reagent supplier. Materials used in the following examples, if no source of purchase is provided, are conventional products that can be commercially available.

The concentrate of culture supernatant of mesenchymal stem cells used in the following examples is prepared as follows:

Human umbilical cord mesenchymal stem cells isolated from a fresh umbilical cord tissue of a healthy newborn by natural or cesarean section delivery are inoculated into a T175 cell culture flask at a density of $2\times10^4$ cells/cm$^2$, and cultured for 48 hours (then 70% confluence is achieved) after adding 25 ml of the serum-free medium, and then the fresh culture supernatant of the umbilical cord mesenchymal stem cells is collected; and the serum-free medium comprises 0.1 part by volume of β-mercaptoethanol, 1 part by volume of aqueous solution of non-essential amino acids (11140, Gibco), 94 parts by volume of a-MEM/DMEM-F12 and the recombinant human basic fibroblast growth factor at a final concentration of 10 ng/ml.

The culture supernatant is centrifuged at 3000 g for 30 min at 4° C., to remove cells and cellular debris suspended therein;

The supernatant obtained by centrifugation is transferred to a new centrifuge tube and centrifuged at 10000 g for 50 min at 4° C., to remove cytoplasm and other impurities in the supernatant.

The supernatant is recovered and filtered through a 0.22 μm microfiltration membrane, to sterilize the supernatant.

The obtained filtrate is transferred to a 3 KD ultrafiltration concentrator tube, and centrifuged at 3000-4500 g for 80 min at 4° C., to concentrate the filtrate to 1/30 of its original volume.

The concentrate obtained is adjusted with PBS to get a final volume of 1/20 of the volume of the initially collected culture supernatant.

EXAMPLE 1

Screening for the Composition of the Medium (i) Screening for the Content of β-mercaptoethanol Medium to be tested: 0.01, 0.02, 0.05, 0.1, 0.15, 0.2, 0.3 or 0.5 parts by volume of β-mercaptoethanol, 10 ng/ml recombinant human basic fibroblast growth factor (b-FGF, Peprotech), 1 part by volume of aqueous solution of non-essential amino acids (11140, Gibco), 5 parts by volume of the concentrate of culture supernatant, and 94 parts by volume of a-MEM.

In a biosafety cabinet, the third generation hUC-MSCs isolated from Wharton's jelly tissue of umbilical cord of a newborn by natural delivery were inoculated into a T75 cell culture flask at a density of $2\times10^4$ cells/cm$^2$, then 12-15 ml of the medium to be tested were added in and the growth of the cells was observed.

Figure 1:
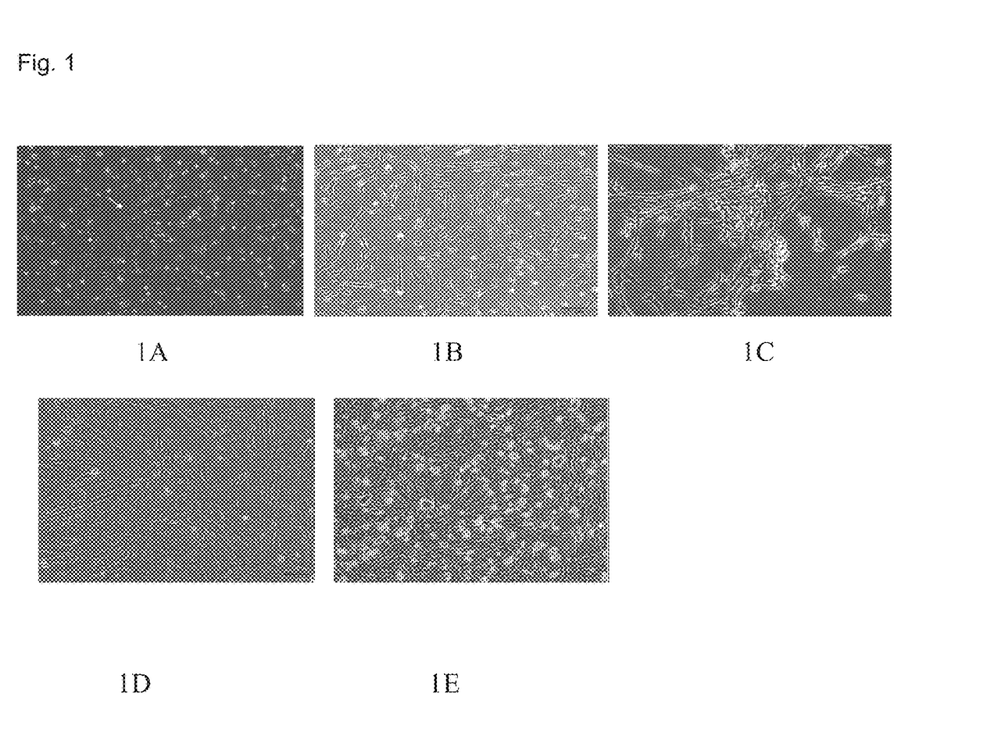
FIG. 1 shows cell images obtained during screening for the composition of the medium, in which penal 1A shows cellular morphology of cells cultured in a high-concentration β-mercaptoethanol medium for 4 hours after inoculation; penal 1B shows cellular morphologies of cells cultured in a low-concentration bFGF medium for 24 hours after inoculation; penal 1C shows cellular morphologies of cells passaged from cells cultured in high-concentration bFGF medium; penal 1D shows cellular morphologies of cells cultured in medium comprising low-concentration concentrate of culture supernatant; and penal 1E shows cellular morphologies of cells cultured in medium comprising high-concentration concentrate of culture supernatant.

Results: The cells in the two concentration groups, i.e. medium comprising 0.01 or 0.02 parts by volume of β-mercaptoethanol respectively, adhered to the walls at a slower rate. Some of the cells still did not adhere to the walls 4 hours after inoculation and nearly all the cells were observed to have adhered about 8 hours after inoculation. The cells in the four concentration groups, i.e. the medium comprising 0.05, 0.1, 0.15 or 0.2 parts by volume of β-mercaptoethanol respectively, adhered to the walls completely 4 hours after inoculation, and bright cells with tentacles stretched out were observed. The cells in the two concentration groups, i.e. the medium comprising 0.3 or 0.5 part by volume of β-mercaptoethanol respectively, had adhered to the walls 4 hours after inoculation, but some of the cells were in poor state and showed symptoms of early differentiation (see panel 1A).

(ii) Screening for the Content of Recombinant Human Basic Fibroblast Growth Factor Medium to be tested: 0.1 part by volume of β-mercaptoethanol, 1, 2, 5, 8, 10, 12, 15, 18, or 20 ng/ml recombinant human basic fibroblast growth factor (b-FGF, Peprotech), 1 part by volume of aqueous solution of non-essential amino acids (11140, Gibco), 5 parts by volume of the concentrate of culture supernatant, and 94 parts by volume of a-MEM.

With reference to the method as described in part (i) above, cells from the same cell source were inoculated at the same density, then 12-15 ml of the medium to be tested was added in and the growth of the cells was observed.

Results: The cells in the two concentration groups, i.e. medium comprising 1 or 2 ng/ml bFGF respectively proliferated slowly and were in poor and undernourished state (see panel 1B). In the concentration groups, i.e. medium comprising 5, 8, 10, 12 or 15 ng/ml bFGF respectively, the cells grew normally, and had high brightness and good growth status. In the concentration groups, i.e., medium comprising 18 or 20 ng/ml bFGF respectively, well proliferating and bright cells were observed. However, the cells were prone to differentiate, clustered into a mass, or had longer tentacles after several passages (see panel 1C).

(iii) Screening for the Content of the Concentrate of Culture Supernatant

Medium to be tested: 0.1 part by volume of β-mercaptoethanol, 10 ng/ml recombinant human basic fibroblast growth factor (b-FGF, Peprotech), 1 part by volume of aqueous solution of non-essential amino acids (11140, Gibco), 1, 2, 4, 5, 6, 8 or 10 parts by volume of the concentrate of culture supernatant, and 94 parts by volume of a-MEM.

With reference to the method described in part (i) above, cells from the same cell source were inoculated at the same density, then 12-15 ml of the medium to be tested was added in and the growth of the cells was observed.

Results: The cells in the two concentration groups, i.e. medium comprising 1 or 2 part(s) by volume of the concentrate of culture supernatant respectively proliferated slowly. When observed 48 hours after inoculation, some of the hUC-MSCs became flat and stopped proliferating when about 60% confluence was achieved (see panel 1D). The cells in the three concentration groups, i.e. medium comprising 4, 5 or 6 parts by volume of the concentrate of culture supernatant respectively had good growth state. 24 hours after inoculation, it was observed that the hUC-MSCs appeared as spindle-shape and gathered in whorls spreading much more, and the cells were bright, and 40-60% confluence was reached; and subsequent observation 48 hours after inoculation showed that the hUC-MSCs were bright and more than 90% confluence was reached. The cells in the two concentration groups, i.e. medium comprising 8 or 10 parts by volume of the concentrate of culture supernatant respectively showed localized inhomogeneous aggregation. Meanwhile, floating things appeared in the culture flask, indicating that part of the cells died (see panel 1E).

EXAMPLE 2

Preparation and Application of the Serum-Free Medium

Preparation of the Serum-Free Medium:
Composition: 0.1 part by volume of β-mercaptoethanol, 1 part by volume of aqueous solution of non-essential amino acids (11140, Gibco), 5 parts by volume of the concentrate of culture supernatant, 94 parts by volume of a-MEM/DMEM-F12 and the recombinant human basic fibroblast growth factor at a final concentration of 10 ng/ml.

A premixture was prepared using the β-mercaptoethanol, aqueous solution of non-essential amino acids and a-MEM/DMEM-F12, and then mixed with the concentrate of culture supernatant and the recombinant human basic fibroblast growth factor.

Figure 2:
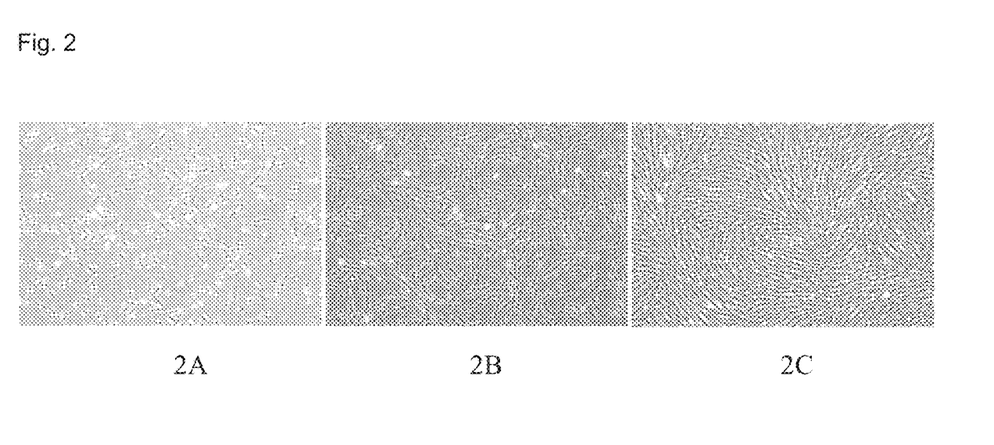
FIG. 2 shows images of umbilical cord mesenchymal stem cells cultured by use of the present serum-free medium, in which penal 2A shows cellular morphology 2 hours after inoculation; penal 2B shows cellular morphology 24 hours after inoculation; and penal 2C shows cellular morphology 48 hours after inoculation.

Culture of cells: In a biosafety cabinet, the third generation hUC-MSCs isolated from Wharton's jelly tissue of umbilical cord of a newborn by natural delivery were inoculated into a T75 cell culture flask at a density of 2×10$^4$ cells/cm$^2$, then the flask was transferred to a constant temperature incubator at 37° C., 5% $CO_2$ after 15 ml of the medium to be tested was added in. The cells were observed to adhere to the walls 2 hours after inoculation, further cultured and then were observed to have completely adhered about 4 hours later. 24 hours after inoculation, it was observed that the hUC-MSCs appeared as spindle-shape and gathered in whorls spreading much more, and the cells were bright, and 40-60% confluence was reached; and subsequent observation 48 hours after inoculation showed that the hUC-MSCs were bright and above 90% confluence was reached. The cells were digested by trypsin, collected and cryopreserved. See FIG. 2 for results.

EXAMPLE 3

Preparation and Application of the Serum-Free Medium

Preparation of the Serum-Free Medium:
Composition: 0.05 part by volume of β-mercaptoethanol, 2 parts by volume of aqueous solution of non-essential amino acids, 4 parts by volume of the concentrate of culture supernatant, 90 parts by volume of DMEM-F12 and the recombinant human basic fibroblast growth factor at a final concentration of 15 ng/ml.

The serum-free medium was prepared according to the method as described in Example 2.

With reference to the method of culturing cells as described in Example 2, good state and 40% confluence were observed for the cells 24 hours after inoculation. With further culture, the cells appeared as spindle-shape and gathered in whorls and 80% confluence was reached 48 hours after inoculation. With continued, the cells did not roll up.

EXAMPLE 4

Preparation and Application of the Serum-Free Medium

Preparation of the Serum-Free Medium:
Composition: 0.2 part by volume of β-mercaptoethanol, 0.5 parts by volume of aqueous solution of non-essential amino acids, 6 parts by volume of the concentrate of culture supernatant, 95 parts by volume of a-MEM and the recombinant human basic fibroblast growth factor at a final concentration of 5 ng/ml.

The serum-free medium was prepared according to the method as described in Example 2.

With reference to the method of culturing cells as described in Example 2, the cells were substantially adherent 4 hours after inoculation and shown as bright circular spot. And 24 hours after inoculation, the cells were in good state and began to converge in whirlpools with a confluence of 30-50%. The cells were cultured continuously and bright cells with tentacles stretched out naturally were observed and 80% confluence was reached 48 hours after inoculation.

EXAMPLE 5

Influence of Different Media on Cell Doubling

Medium to be Tested:
Serum-free medium of the present invention (SCL-M): 94 parts by volume of a-MEM/DMEM-F12, 0.1 part by volume of β-mercaptoethanol, 1 part by volume of aqueous solution of non-essential amino acids (11140, Gibco), 5 parts by volume of the concentrate of culture supernatant and the recombinant human basic fibroblast growth factor at a final concentration of 10 ng/ml.

Medium comprising serum (FBS): 89 parts by volume of a-MEM/DMEM-F12, 0.1 part by volume of β-mercaptoethanol, 1 part by volume of aqueous solution of non-essential amino acids (11140, Gibco), 10 parts by volume of FBS and the recombinant human basic fibroblast growth factor at a final concentration of 10 ng/ml.

Serum-free medium with addition of conventional serum substitute (SR): 89 parts by volume of a-MEM/DMEM-F12, 0.1 part by volume of β-mercaptoethanol, 1 part by volume of aqueous solution of non-essential amino acids (11140, Gibco), 10 parts by volume of serum substitute (available from Gibco under Catalog No. 10828-010) and the recombinant human basic fibroblast growth factor at a final concentration of 10 ng/ml.

The first generation cells cultured in Example 2 were inoculated into a 6-well plate at a density of $2 \times 10^4$ cells/cm$^2$, 2 ml of each of the above three kinds of tested media was added to each well respectively, and after 48 hours culture, the cells were digested by trypsin and the total number of cells in the 6 wells was calculated. The cells were further inoculated in another 6-well plate at the same density and the same procedures were repeated until the cells were cultured to 21 passages. Make 2 replicates for each kind of medium.

Calculation of cumulative population doubling:

(1) Population doubling $(PD)=[\log_{10}(N_H)-\log_{10}(N_0)]/\log_{10}(2)$; wherein $N_H$ represents the number of cells collected, and $N_0$ represents the number of cells inoculated.

(2) cumulative population doubling (CPD) represents sum of PDs obtained from continuous passage.

Figure 3:
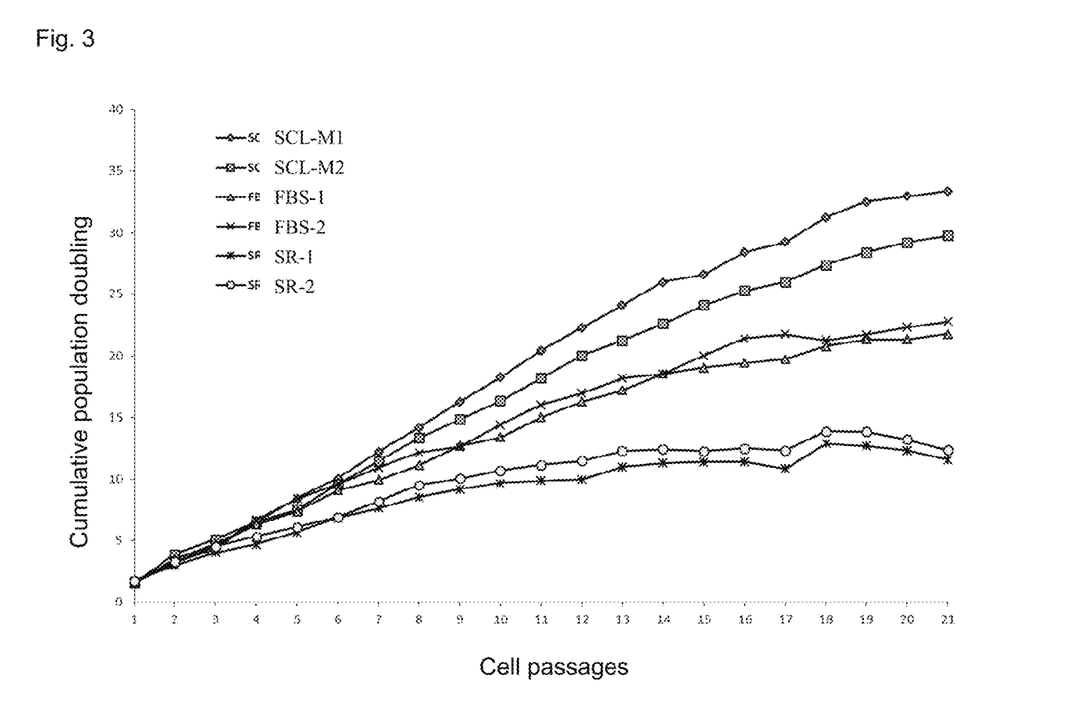
FIG. 3 shows results of doubling curve, which is drawn using data obtained from continuous passage of hUC-MSCs in the present serum-free medium verus other media, indicating that the hUC-MSCs cultured in the serum-free medium of the present invention can maintain high proliferation rate in a long-term culture. In the figure, SCL-M1 and SCL-M2 belong to the group of serum-free medium of the present invention, FBS-1 and FBS-2 belong to the group of medium in which serum is added, and SR-1 and SR-2 belong to the group of medium in which commercially available serum-substitute is added.

The results were shown in FIG. 3. The high passage cells (P21) (groups of SCL-M1 and SCL-M2) still maintained good expansion effect when conducting continuous passage culture by use of the present serum-free medium. While, when conducting continuous passage culture by use of the medium comprising serum, proliferation of the cells slowed down significantly at the 13th generation (groups of FBS-1 and FBS-2). When culture medium with addition of conventional serum substitute was used (groups of SR-1 and SR-2), the proliferation rate of the cells was relatively stable but slower than other groups.

EXAMPLE 5

Analysis of Cell Viability and Growth Characteristics of hUC MSCs by Cell Viability Analyzer The third generation cells cultured in Example 2 were inoculated into a T25 culture flask, and when 95%-100% confluence was reached, the cells were digested by 0.125% trypsin, collected and inoculated into two 6-well plates at a density of $1 \times 10^5$ cells/cm$^2$. After all the cells had adhered and partially grown for 10 hours, cells in two wells were collected and prepared into a cell suspension by addition of 500 μL of PBS which was then analyzed on a cell viability analyzer (Cell Viability Analyzer Vi-Cell XR, Beckman). After that, sampling and analysis were conducted every 12 hours and the growth curve was drawn accordingly.

Figure 4:
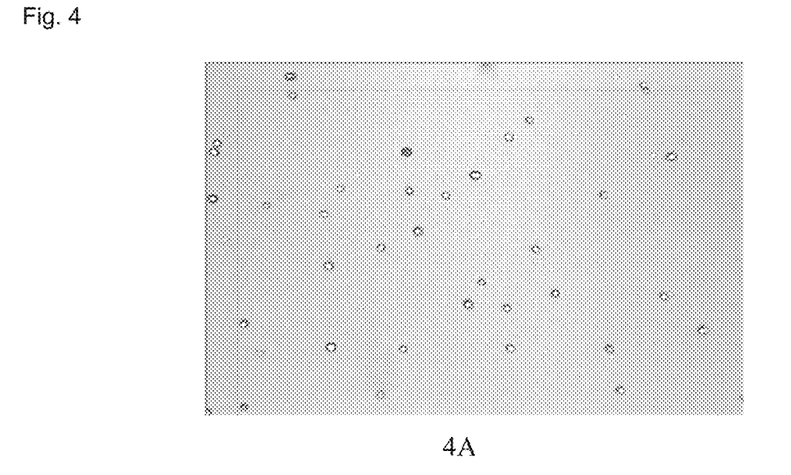
FIG. 4 shows the analysis results of cell viability and growth characteristics of the obtained umbilical cord mesenchymal stem cells by the Vi-Cell cell viability analyzer, in which panel 4A shows the real-time viability of hUC-MSCs; and panel 4B shows the diameter distribution of hUC-MSCs, indicating the viability of hUC-MSCs is above 99% and the cell diameter distribution is around 9-15 μm.

Results shown in FIG. 4 indicated that the viability of hUC-MSCs was above 99.7% and the cell diameter distribution was around 9-15 μm. The hUC-MSCs appeared as spindle-shape and grew in whorls had a complete roundness after digestion. Meanwhile the cells had proliferation characteristics of latent period, logarithmic growth period and plateau period.

EXAMPLE 6

Analysis of Surface Markers of the hUC-MSCs by Flow Cytometry

Figure 5:
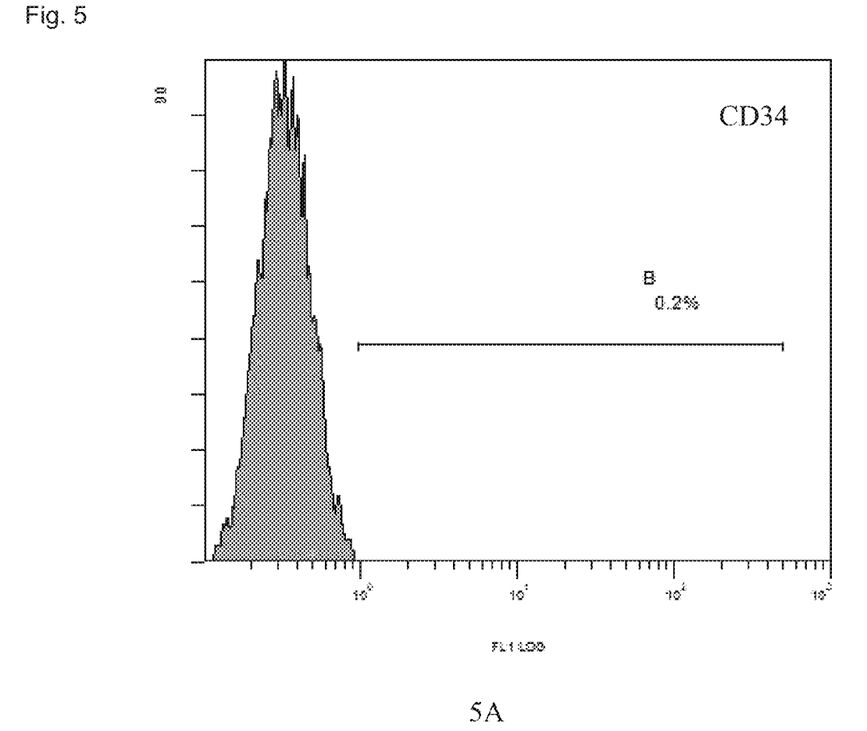
FIG. 5 (panels 5A to 5I) shows the analysis results of cell surface molecules by flow cytometry, indicating that the hUC-MSCs expressed CD29, CD44, CD73, CD90, CD105 and HLA-ABC with ratios of positive cells greater than 99%; and the hUC-MSCs expressed CD45, CD34 and HLA-DR with ratios of positive cells less than 1%.

The third generation cells cultured in Example 2 were inoculated and digested by 2 mL 0.125% trypsin when 90% confluence was reached, and then centrifuged at 1200 rpm for 6 minutes at 4° C. The supernatant was discarded and the cells were collected and washed twice with PBS. The cells were then transferred to a flow tube in an amount of $1 \times 10^5$ cells per tube, and 5 μL of each of CD34-PE, CD45-FITC, CD29-FITC, CD44-PE, CD73-PE, CD105-PE, CD90-FITC, HLA-ABC-FITC, HLA-DR-PE, IgG1-PE (isotype control), and IgG1-FITC (isotype control) antibodies was added into the tube respectively. The cells were mixed and incubated in dark for 30 minutes at 4° C., washed once with PBS, centrifuged and the supernatant was discarded. The collected cells were resuspended by addition of 500 μL PBS, and then detected on a Flow Cytometer (Flow Cytometer XL, Beckman). $1 \times 10^4$ cells were collected from each sample. The results are shown in FIG. 5, and immunophenotypes of the cells are as follows:

Positive expression (more than 99%): CD29, CD44, CD73, CD105, CD90, HLA-ABC;

Negative expression (less than 1%): CD34, CD45, HLA-DR.

EXAMPLE 7

Identification of Multi-Directional Differentiation Potential of the hUC-MSCs

1) Osteogenic Differentiation

The third generation cells cultured in Example 2 were inoculated into a 6-well cell culture plate at a density of $3 \times 10^4$ cells/cm$^2$, 2 ml of freshly prepared human UC MSC osteogenic differentiation medium (HUXUC-90021, Cyagen) was added into per well after 24 hours, and the medium was replaced with fresh osteogenic differentiation medium every 3 days thereafter. Two weeks later, the cells were fixed with paraformaldehyde, and stained with alizarin red for 3-5 minutes.

Figure 6:
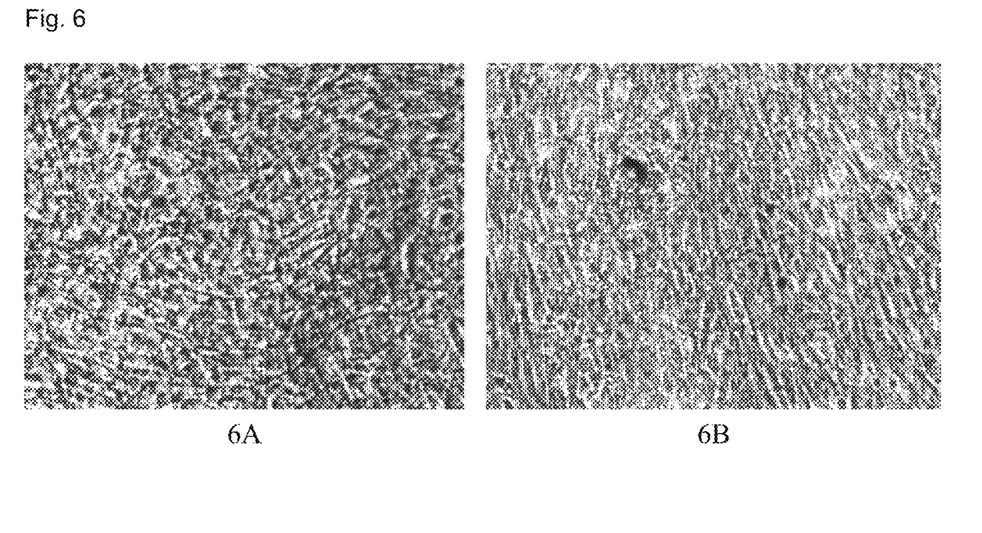
FIG. 6 shows the directed induced differentiation of the obtained hUC-MSCs into osteogenic and adipogenic cells, in which panel 6A shows dark red compounds produced by a chromogenic reaction between alizarin red and calcium nodules during osteogenesis, and panel 6B shows the specific oil red O staining of the fat droplets in adipogenic cells.

The results shown in panel 6A indicated that after two weeks of osteogenic induction on hUC MSCs obtained by culture with the medium of present invention, a dark red chromogenic reaction between the alizarin red and calcium nodules during osteogenesis took place.

2) Adipogenic differentiation

The third generation cells cultured in Example 2 were inoculated into a 6-well cell culture plate at a density of $2 \times 10^4$ cells/cm$^2$. When 100% confluence had reached, fresh liquid A of adipogenic differentiation medium (HUXUC-90031, Cyagen) was added to each well to start induction. Three days later, the liquid A was replaced with liquid B of adipogenic differentiation medium and the culture was maintained for 24 hours. So the cycle continued until more but fairly small fat droplets appeared, then the culture system was maintained for 7 day with liquid B of adipogenic differentiation medium. When the induction ended, the cells were fixed with 4% paraformaldehyde and stained with Oil red O.

The results shown in penal 6B indicated that the lipoblasts were stained significantly by Oil red O after two weeks of adipogenic induction on hUC MSCs cultured by the present medium.

The above description for the embodiments of the present invention is not intended to limit the present invention, and those skilled in the art can make various changes and variations according to the present invention, which are within the protection scope of the present invention without departing from the spirit of the same.

What claimed is:

1. A serum-free medium for expansion culture of human umbilical cord mesenchymal stem cells (hUC-MSCs) in vitro, wherein the serum-free medium consists of 90-95 parts by volume of a-MEM or DMEM-F12, 0.05-0.2 parts by volume of β-mercaptoethanol, 0.5-2 parts by volume of aqueous solution of non-essential amino acids, recombinant human basic fibroblast growth factor (b-FGF) at a final concentration of 5-15 ng/ml and 4-6 parts by volume of a concentrate of culture supernatant of human umbilical cord mesenchymal stem cells (hUC-MSCs), wherein the aqueous solution of non-essential amino acids comprises glycine, alanine, L-asparagine, L-aspartic acid, glutamic acid, proline and serine, each at a concentration of 8-12 mM, wherein the concentrate of culture supernatant is produced by a method consisting of the following steps:

(1) inoculating human umbilical cord mesenchymal stem cells in a serum-free medium at a density of $0.5$-$4 \times 10^4$ cells/cm$^2$ and culturing the cells for 48-72 hours to allow the cells to reach 70%-90% confluence, and then collecting fresh culture supernatant of the umbilical cord mesenchymal stem cells;

(2) centrifuging the culture supernatant at 3000-5000 g for 15-40 min at 4° C., to remove cells and cellular debris suspended therein;

(3) centrifuging the supernatant obtained from step (2) at 10000 g for 30-60 min at 4° C., to remove cytoplasm and other impurities therein;

(4) filtering the supernatant obtained from step (3) through a 0.22 μm microfiltration membrane, to sterilize the supernatant;

(5) transferring a filtrate obtained from step (4) to a 3 KD ultrafiltration concentrator tube, and centrifuging at 3000-4500 g for 60-90 min at 4° C., to concentrate the filtrate to 1/20 to 1/50 of its original volume; and (6) adjusting the concentrate obtained from step (5) with PBS to get a final volume of 1/20 of the volume of the culture supernatant collected in step (1), wherein the serum-free medium in step (1) consists of 0.05-0.2 parts by volume of β-mercaptoethanol, 0.5-2 parts by volume of aqueous solution of non-essential amino acids, 90-95 parts by volume of a-MEM or DMEM-F12, and recombinant human basic fibroblast growth factor at a final concentration of 5-15 ng/ml, and the aqueous solution of non-essential amino acids comprises glycine, alanine, L-asparagine, L-aspartic acid, glutamic acid, proline and serine each at a concentration of 8-12 mM.

2. The serum-free medium according to claim 1, wherein the serum-free medium consists of 0.1 part by volume of β-mercaptoethanol, 1 part by volume of aqueous solution of non-essential amino acids, 5 parts by volume of the concentrate of culture supernatant, 94 parts by volume of a-MEM or DMEM-F12 and the recombinant human basic fibroblast growth factor at a final concentration of 10 ng/ml.

3. The serum-free medium according to claim 1, wherein in step (1), the human umbilical cord mesenchymal stem cells (hUC-MSCs) are human umbilical cord mesenchymal stem cells isolated from a fresh umbilical cord tissue of a healthy newborn by natural or cesarean section delivery.

4. A method for preparing the serum-free medium according to claim 1, wherein the method includes collecting a culture supernatant of human umbilical cord mesenchymal stem cells by performing the steps (1)-(6) of claim 1, to obtain a concentrate of the culture supernatant;

preparing a premixture using β-mercaptoethanol, non-essential amino acids and a-MEM or DMEM-F12; and mixing the concentrate of the culture supernatant, the premixture and recombinant human basic fibroblast growth factor.

5. The serum-free medium according to claim 1, wherein the serum-free medium in step (1) consists of 0.1 part by volume of β-mercaptoethanol, 1 part by volume of aqueous solution of non-essential amino acids, 94 parts by volume of a-MEM or DMEM-F12 and the recombinant human basic fibroblast growth factor at a final concentration of 10 ng/ml.

* * * * *